United States Patent [19]
Kurkov

[11] 3,932,468
[45] Jan. 13, 1976

[54] DIHYDROFURAN PREPARATION
[75] Inventor: Victor P. Kurkov, San Rafael, Calif.
[73] Assignee: Chevron Research Company, San Francisco, Calif.
[22] Filed: Feb. 8, 1974
[21] Appl. No.: 440,937

[52] U.S. Cl.... 260/346.1 R; 252/431 R; 252/431 C
[51] Int. Cl.$^2$.................................... C07D 307/08
[58] Field of Search................................ 260/347.1

[56] References Cited
UNITED STATES PATENTS
3,812,158   5/1974   Besozzi et al.................... 260/347.1

Primary Examiner—Harry I. Moatz
Attorney, Agent, or Firm—G. F. Magdeburger; John Stoner, Jr.; T. G. DeJonghe

[57] ABSTRACT

A process for preparing a substituted or unsubstituted dihydrofuran from a substituted or unsubstituted butadiene monoxide which comprises contacting the butadiene monoxide with a catalyst comprising a hydrogen halide selected from the group consisting of hydrogen iodide or bromide and a homogeneous transition metal compound in an organic solvent under conditions effective to convert the butadiene monoxide to the dihydrofuran and wherein said transition metal compound is effective to accelerate said conversion. Preferably the transition metal is iron, manganese, cobalt, molybdenum, vanadium, copper, or nickel.

10 Claims, No Drawings

DIHYDROFURAN PREPARATION

BACKGROUND OF THE INVENTION

The present invention relates to preparation of 2,5-dihydrofuran from butadiene monoxide. The dihydrofuran can be hydrogenated to tetrahydrofuran, which is a good solvent for high-molecular polyvinyl chloride, polyvinylidene chloride, and other difficultly soluble organic materials.

Closely related compounds can be prepared from 2,5-dihydrofuran. 2,3-dihydrofuran can be obtained by isomerizing 2,5-dihydrofuran (see, for example, U.S. Pat. No. 2,556,325); and tetrahydrofuran is readily produced from a dihydrofuran by hydrogenation.

Prior methods for preparation of tetrahydrofuran include catalytic hydrogenation of furan, which, in turn, can be prepared by decarbonylation of furfural (see, for example, U.S. Pat. Nos. 2,374,149 and 2,846,449). Furfural in the past has been produced from naturally occurring various vegetable materials such as corn cobs and oat hulls.

In addition to obtaining tetrahydrofuran from furfural as a source material, tetrahydrofuran can also be produced by heating 1,4-butylene glycol — for example, in an over-all process using acetylene as the starting material and having the following steps:

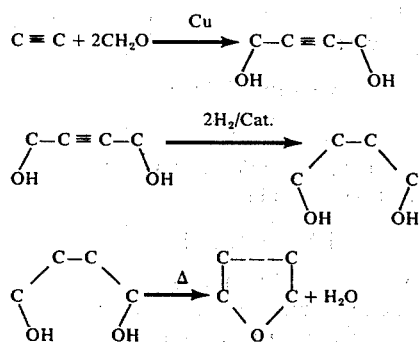

Relating to the production of tetrahydrofuran from 1,4-butylene glycol by heating under specified conditions, see the disclosures of, for example, Reppe et al U.S. Pat. Nos. 2,251,292, 2,251,835, and 2,251,895; and also Rogers U.S. Pat. No. 3,467,679.

Production of tetrahydrofuran by hydrogenation of maleic anhydride is described by T. Yoshimura in *Chemical Engineering*, 1969, at page 70.

Oxidation of 1,3-butadiene to furan using a catalyst such as manganese molybdate is disclosed in U.S. Pat. No. 2,900,396. Oxidation of various organic compounds to furan using a bismuthmolybdenum catalyst at a temperature of at least 350°C. is disclosed in U.S. Pat. No. 3,600,405. Crotonaldehyde (propylene aldehyde) is a preferred feedstock in the process of U.S. Pat. No. 3,600,405; other feedstocks disclosed are acetals and hemi-acetals of crotonaldehyde, aldol, butadiene monoxide, crotyl alcohol, n-butyl alcohol, 1,4-butanediol and n-butyraldehyde.

The present invention is particularly concerned with preparation of dihydrofuran from an epoxide by rearrangement. An example of an epoxide rearrangement is disclosed by Heap et al. in the *Journal of the American Chemical Society*, 1969, at page 160. Heap et al reported that 1,3-cyclooctadiene oxide was rearranged in the presence of perchloric acid to 9-oxabicyclo(2,4,1)-non-7-ene in about 50 percent yield:

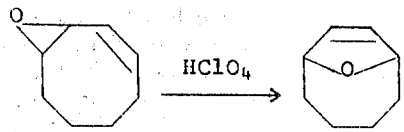

SUMMARY OF THE INVENTION

According to the present invention a process is provided for preparing a substituted or unsubstituted dihydrofuran from a substituted or unsubstituted butadiene monoxide, which process comprises contacting the butadiene monoxide with a catalyst comprising a hydrogen halide selected from the group consisting of hydrogen iodide or bromide and a homogeneous transition metal compound in an organic solvent under conditions effective to convert the butadiene monoxide to the dihydrofuran and wherein said transition metal compound is effective to accelerate said conversion.

Among other factors, the present invention is based on my discovery that butadiene monoxide can be converted to 2,5-dihydrofuran using hydrogen iodide or hydrogen bromide and certain effective transition metal catalysts and that unexpectedly high yields of 2,5-dihydrofuran are achieved in such process.

Preferably the process of the present invention is used to produce 2,5-dihydrofuran which does not have substituents attached thereto, i.e. unsubstituted dihydrofurans. However, substituted dihydrofurans can also be produced by the method of the present invention. The terminology "substituted dihydrofurans" or "substituted butadiene monoxide" is used to connote that the basic dihydrofuran or butadiene monoxide structure has a substituent attached onto it as, for example, an alkyl group attached onto the basic dihydrofuran or butadiene monoxide structure. For instance, I have found that 1,2-epoxy-2-methyl-3-butene and 1,2-epoxy-3-methyl-3-butene can be converted to 3-methyl-2,5-dihydrofuran using an iron transition metal catalyst and hydrogen iodide. Preferred substituted butadiene monoxide feedstocks for producing substituted dihydrofuran are substituted butadienes having one or more alkyl groups containing 1-8 carbon atoms which could also be part of a ring, such as 1,3-pentadiene, 1,3-hexadiene, 2,3-dimethyl-1,3-pentadiene, 1,3-octadiene, cyclopentadiene, 1,3-cyclooctadiene, 1,3-cyclododecatriene, etc; substituted butadienes having one or more halogens, such as chloroprene, 2,3-dichlorobutadiene, 1,4-dichlorobutadiene, 1,1-dichlorobutadiene, and bromoprene.

Preferably the reaction is carried out in liquid phase using an organic solvent such as N-methyl-pyrrolidone. Suitable organic solvents for the present invention are inert organic media such as substituted amides, hydrocarbons and chlorinated hydrocarbons, i.e., N-methyl-pyrrolidone, benzene, xylenes, hexane, chlorobenzene, etc.

I have found that certain amines will react in the reaction system of the present invention — these amines are not suitable for the process of the present invention. Such amines in particular include N-methyl-pyrrolidine and 2,6-dimethylpiperidine. These latter-type organic compounds are believed to react with iodo- or bromohydrin compounds in the reaction system — in particular they are believed to be alkylated by the halohydrin compound.

Thus, preferably the inert organic solvent used in the present invention is a solvent which is not readily alkylated under the reaction conditions of the present process. Tertiary amides, i.e., amides which have both the hydrogen groups substituted by organic radicals, are especially preferred inert organic media. Particularly preferred tertiary amides for use herein are N-methylpyrrolidone, N,N-dimethylformamide, N,N-dimethylacetamide, etc.

The transition metal catalyst used in the present invention is a homogeneous catalyst, as opposed to a heterogeneous catalyst, and thus the transition metal should be coordinated with suitable ligands to solubilize the transition metal in the organic reaction medium. For example, iron having a valence of +3 [iron(III)] coordinated with acetylacetone was found to be especially effective, as was ferric 2-ethylhexanoate. In these latter two cases the iron(III) is, of course, coordinated with three of the organic ligands. In general, the ligand coordinated with the transition metal can be substantially any organic ligand which will solubilize the transition metal in the organic reaction medium.

Preferred transition metal catalysts are those wherein the transition metal is iron, manganese, cobalt, molybdenum, vanadium, copper or nickel. Of these transition metals, iron and manganese have been found to give the highest yields.

Although I have in general found the ligands to which the transition metal is coordinated not to be of special importance, I have found the valence of the transition metal to be important in many instances. Thus I have found iron(III) to give unexpectedly higher yields of the dihydrofuran than are obtained using iron(III) or iron(0). Also, manganese(II), which is isoelectronic with iron(III), gives high yields of the dihydrofuran. Particularly preferred transition metals and their valences are iron(III), iron(II), cobalt(II), molybdenum-(II), vanadium(III), manganese(II) and nickel(II). Of these, iron(III) and manganese(II) are the most preferred. The preferred amount of transition metal catalyst varies from 0.01 to 0.3, preferably 0.02 to 0.1, mols per mol of butadiene monoxide.

Preferably the hydrogen halide used in the present invention is hydrogen iodide. Preferred molar ratios of the hydrogen halide to butadiene monoxide are 0.01 to 1:1, and especially preferred ratios are 0.03 to 0.3:1.

Preferred reaction temperatures for the process of the present invention are between 50° and 140°C., and especially preferred temperatures are between 80° and 120°C. The reaction is normally carried out in liquid phase and thus a pressure is usually maintained sufficient to retain liquid phase. Usually the pressure is between about 1 atmosphere and 60 atmospheres, and preferably between about 1 and 30 atmospheres.

EXAMPLES

EXAMPLE 1

77 g (778 mmol) N-methylpyrrolidone (NMP) was placed in a 250-ml round-bottomed flask provided with a thermometer and a reflux condenser. The flask was cooled in dry-ice acetone and charged with 4.9 g (38 mmol) of hydrogen iodide (HI) gas, 32 g (453 mmol) of butadiene monoxide (BDMO), added dropwise, and 3.5 g (10 mmol) of ferric acetylacetonate (Fe[AcAc]₃). The reaction was heated at 88°C. (90°C. bath) under reflux for 3½ hours. Gas-liquid partition chromatograph (GLPC) analysis showed 100 percent conversion and 78 percent yield of 2,5-dihydrofuran. The product (21 g) was recovered by distillation through a 6 inch packed column — boiling point 62°–68°C. (literature 68°C.); 89 percent pure by GLPC; nuclear magnetic resonance (NMR) (CCl₄): δ 4.5 ppm (s) 4H, 5.83 ppm (s) 2H (vinyl). The infrared (IR) spectrum was identical with that of a reference sample of dihydrofuran.

EXAMPLES 2–4

Table I

The procedure of Example 1 was followed, using 153 millimols (mmols) of NMP, 70 mmols of BDMO, 7 mmols of HI (except Example 3), and 1 mmol of ferric acetylacetonate (except Example 4).

EXAMPLES 5–11

Table II

The procedure of Examples 2–4 was followed, using different solvents.

EXAMPLES 12–26

Table III

The procedure of Examples 2–4 was followed, but varying the catalyst.

EXAMPLES 27–30

Table IV

The procedure of Examples 2–4 was followed, but varying the hydrogen halide.

EXAMPLE 31

Isoprene oxides (4.7 g, 53 mmols) — 4.4:1 mixture of 3,4-epoxy-3-methyl-1-butene and 3,4-epoxy-2-methyl-1-butene were rearranged in 15 g of NMP containing 0.94 g (7.3 mmols) of HI and 0.7 g (2 mmols) of ferric acetylacetonate, as described above for BDMO. 3-Methyl-2,5-dihydrofuran was obtained in 42 percent yield. Hydrogenation of the product over a palladium-on-carbon catalyst gave 3-methyltetrahydrofuran identical with an authentic sample.

EXAMPLE 32

8.7 g (70 mmols) of cyclooctadiene oxide, 15.1 g of NMP, 0.82 g of HI (7 mmols) and 0.7 g of ferric acetylacetonate (2 mmols) were reacted at 90°C. for ½ hour. Conversion was 100 percent, and the yeild of 9-oxabicyclo(4,2,1)non-7-ene was 79 percent.

TABLE I

| | | Control Runs | | | | |
|---|---|---|---|---|---|---|
| Ex. No. | Catalyst | Temp., °C. | Time, hrs | Conversion, % | Initial Rate, %/Hr | DHF Yield,** Mol % |
| 2 | Fe(AcAc)₃/HI | 92 | 2.25 | 100 | 43 | 93 |
| 3* | Fe(AcAc)₃ | 107 | 10 | 18 | 1.8 | 0 |
| 4 | HI | 92 | 2 | 35 | 17 | 33 |

| Charge | mmols |
|---|---|
| Butadiene monoxide | 70 |
| N-methylpyrrolidone | 153 |
| Hydrogen iodide | 7 |

TABLE I-continued

Control Runs

| Ex. No. | Catalyst | Temp., °C. | Time, hrs | Conversion, % | Initial Rate, %/Hr | DHF Yield,** Mol % |
|---|---|---|---|---|---|---|
| | Fe(AcAc)₃ | | | | | 1 |

*One-half scale
**Based on converted BDMO (GLPC, internal standard)

TABLE II

Effect of Solvent

| Ex. No. | Solvent | Time,* hrs | Rate,# %/hr | DHF Yield,** mol % |
|---|---|---|---|---|
| 5 | N-methylpyrrolidone | 2 | 50 | 87 |
| 6 | ##Benzene | 10 | — | 18 |
| 7 | N-methylpyrrolidone/Benzene = 1 | 3 | 30 | 82 |
| 8 | N-methylpyrrolidone/Benzene = 0.5 | 3 | 24 | 85 |
| 9 | N,N-dimethylformamide | <5 | 73 | 47 |
| 10 | N-methylpyrrolidine | — | — | 0 |
| 11 | 2,6-dimethylpiperidine | — | 8 | 0 |

| Charge | mmols |
|---|---|
| Butadiene monoxide | 70 |
| Solvent | 15 ml |
| HI | 7 |
| Fe(AcAc₃) | 2 |

*For 100% conversion at 90°C.
**As in Table I
For first 60 minutes
1 mmol Fe(AcAc)₃ at 100°C.

TABLE III

Effect of Catalyst

| Ex. No. | Catalyst | Time, hrs | Conversion, % | Initial Rate, %/hr | DHF Yield,** mol % |
|---|---|---|---|---|---|
| 12 | Fe(AcAc)₃ | 2.25 | 100 | 43 | 93 |
| 13 | Fe(2EH)₃ | 2 | 92 | 150 | 74 |
| 14 | Fe(AcAc)₂ | 3 | 84 | 47 | 45 |
| 15* | FeI₂ | 1.5 | 39 | 26 | 28 |
| 16 | Fe(CO)₅ | 3.5 | 98 | 59 | 35 |
| 17 | [Fe(Cp)(CO)₂]₂ | 6 | 95 | 34 | 36 |
| 18 | #Mn(AcAc)₂ | 2 | 85 | 63 | 74 |
| 19 | #Co(2EH)₂ | 2.5 | 91 | 58 | 56 |
| 20 | #Mo(AcAc)₂ | 2 | 89 | 57 | 50 |
| 21 | #V(AcAc)₃ | 3.5 | 83 | 40 | 46 |
| 22 | Cu(AcAc)₂ | 3.25 | 61 | 60 | 21 |
| 23 | Ni(AcAc)₂ | 1 | 62 | 62 | 37 |
| 24 | PdCl₂(C₆H₅CN)₂ | 3 | 53 | 38 | 0 |
| 25 | Ru(AcAc)₃ | 3 | 42 | 36 | 0## |
| 26 | None | 22 | 95.5 | 18 | 27 |

| Charge | mmols |
|---|---|
| N-methylpyrrolidone | 150 |
| Hydrogen iodide | 7 |
| Butadiene monoxide | 70 |
| Catalyst | 1 |
| Temperature 92°C. | |

*No HI
**As in Table I
82°C.
Crotonaldehyde was the major product

TABLE IV

Effect of Promoter

| Ex. No. | Promoter | Time, hrs | Conversion, % | Initial Rate, %/hr | DHF Yield** mol % |
|---|---|---|---|---|---|
| 27 | HI | 2.25 | 100 | 43 | 93 |
| 28 | HBr | 18 | 100 | 16 | 18 |
| 29 | 3 × HBr | 3 | 100 | 54 | 40 |
| 30 | 3 × HCl | 6 | 68.5 | 11 | 0 |

| Charge | mmols |
|---|---|
| Butadiene monoxide | 70 |

TABLE IV-continued

Effect of Promoter

| Ex. No. | Promoter | Time, hrs | Conversion, % | Initial Rate, %/hr | DHF Yield** mol % |
|---|---|---|---|---|---|
| | N-methylpyrrolidone | | | 150 | |
| | HX | | | 7 | |
| | Fe(AcAc)₃ | | | 1 | |
| | Temperature 92°C. | | | | |

**As in Table I

What is claimed is:

1. A process for preparing a substituted or unsubstituted dihydrofuran from a substituted or unsubstituted butadiene monoxide which comprises contacting the butadiene monoxide with a catalyst comprising a hydrogen halide selected from the group consisting of hydrogen iodide or bromide and a homogeneous transition metal compound in an inert organic solvent under liquid phase reaction conditions effective to convert the butadiene monoxide to the dihydrofuran, said reaction conditions including a temperature between 50° and 140°C, and wherein said transition metal is iron, manganese, cobalt, molybdenum, vanadium, copper or nickel, and wherein the transition metal is coordinated with suitable organic ligands to solubilize the transition metal in the organic solvent.

2. A process in accordance with claim 1 wherein the dihydrofuran is unsubstituted 2,5-dihydrofuran and the butadiene monoxide is unsubstituted butadiene monoxide.

3. A process in accordance with claim 2 wherein the transition metal is iron or manganese.

4. A process in accordance with claim 2 wherein the transition metal is iron(III), iron(II), cobalt(II), molybdenum(II), vanadium(III) or manganese(II).

5. A process in accordance with claim 2 wherein the transition metal is iron(III).

6. A process in accordance with claim 5 wherein the hydrogen halide is hydrogen iodide.

7. A process in accordance with claim 1 wherein the organic solvent is an inert solvent which is substantially unalkylated under the reaction conditions.

8. A process in accordance with claim 7 wherein the solvent comprises a tertiary organic amide.

9. A process in accordance with claim 8 wherein the solvent is N-methylpyrrolidone or N,N-dimethylformamide or N,N-dimethylacetamide.

10. A process in accordance with claim 6 wherein the solvent is N-methylpyrrolidone or N,N-dimethylformamide or N,N-dimethylacetamide.

* * * * *